United States Patent
Li

(10) Patent No.: US 6,716,984 B2
(45) Date of Patent: Apr. 6, 2004

(54) POLYMER-SUPPORTED SYNTHESIS OF HETEROATOM BIDENTATE LIGANDS FOR CATALYSIS

(75) Inventor: George Y. Li, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 125 days.

(21) Appl. No.: 09/832,405

(22) Filed: Apr. 11, 2001

(65) Prior Publication Data

US 2002/0077479 A1 Jun. 20, 2002

Related U.S. Application Data

(60) Provisional application No. 60/197,031, filed on Apr. 13, 2000.

(51) Int. Cl.$^7$ .................................................. C07F 9/06
(52) U.S. Cl. ......................................................... 546/21
(58) Field of Search ...................... 568/8, 11; 546/21; 548/111; 549/5, 216

(56) References Cited

U.S. PATENT DOCUMENTS

| | | |
|---|---|---|
| 5,530,125 A | 6/1996 | Berger et al. |
| 5,892,091 A | 4/1999 | Harada et al. |
| 6,559,333 B1 * | 5/2003 | Brunelle et al. ............ 558/452 |

FOREIGN PATENT DOCUMENTS

WO    WO 99/52915 A1    10/1999

OTHER PUBLICATIONS

Baranano, D., et al., Carbon–Heteroatom Bond–Forming Reductive Elimination. Mechanism, Importance of Trapping Reagents, and Unusual Electronic Effects During Formation of Aryl Sulfides. J. Am. Chem. Soc., 1995, 2937–2938, 117.

Zheng, N., et al., Palladium–Catalyzed Synthesis of Aryl Sulfides from Aryl Triflates, J. Org. Chem., 1998, 9606–9607, 63.

Broger, E. A., et al., New Amidophosphine–phosphinites (tLANOPs) as Chiral Ligands for Asymmetric Hydrogenation Reactions, Tetrahedron: Asymmetry, 1998, 4043–4054, 9.

Hartley, F. R., Supported Metal Complex Catalysts, Chemistry of the Metal–Carbon Bond, 1987, 1164–1225, 4.

King, R. B., Encyclopedia of Inorganic Chemistry, 3149–3213, 6.

\* cited by examiner

*Primary Examiner*—Zinna Northington Davis
(74) *Attorney, Agent, or Firm*—Inna Y. Belopolsky

(57) ABSTRACT

The invention relates to the combinatorial approaches to the preparation of novel polymer-supported heteroatom bidentate (PN, PO, PS) ligand libraries and the corresponding free compounds after cleavage from the supports. These compounds are useful as novel ligands in the preparation of metal-containing catalysts.

6 Claims, No Drawings

POLYMER-SUPPORTED SYNTHESIS OF HETEROATOM BIDENTATE LIGANDS FOR CATALYSIS

FIELD OF INVENTION

The invention relates to the combinatorial approaches to the preparation of novel polymer-supported heteroatom bidentate (PN, PO, PS) ligand libraries and the corresponding free compounds after cleavage from the supports. These compounds are useful as novel ligands in the preparation of metal-containing catalysts.

BACKGROUND

Chelating phosphine compounds bound to metal atoms are useful as catalysts. To facilitate separation of the catalysts from a chemical process, phosphorus ligands have been attached to solid supports such as polymers. Interest in using the combinatorial "split-and-mix synthesis" approach to generate polymer-bound ligands which could be tested as catalysts has brought to fore the importance of new chemistry with which to attach phosphine ligands to polymer supports.

Novel processes have been discovered to prepare new compositions of matter that contain chelating phosphine compounds, including compounds of asymmetric and unsymmetric diphosphines using solid supports. Phosphine compounds have been shown to be useful when combined with transition metals as catalysts for chemical processes. The processes can also be utilized in a combinatorial scheme to produce libraries of phosphine compounds. These processes and the compounds prepared are described in U.S. patent application Ser. No. 09/415,347, filed Oct. 8, 1999.

Rapid, clean, high-yielding processes are needed, however, in which a variety of phosphine ligands are prepared. Especially needed are processes to prepare heteroatom bidentate phosphine ligands which are difficult to prepare using traditional methods as the intermediates are generally unstable. Processes are also needed that prepare these ligands in a library format and use chiral substituents.

SUMMARY OF INVENTION

The invention is directed towards a process to prepare a supported phosphine compound of Formula 1:

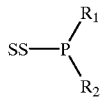

wherein SS is a solid support; $R_1$ is selected from the group consisting of halogen, hydrocarbyl, substituted hydrocarbyl, heterocyclic and substituted heterocyclic; and $R_2$ is selected from the group consisting of halogen, cyclic hydrocarbyl, substituted cyclic hydrocarbyl, heterocyclic and substituted heterocyclic. The process comprises the steps of: a) contacting a phosphine of the formula $XPR_1R_2$, wherein X is a halogen, with the solid support, resulting in the P in the phosphine attached indirectly or directly to the solid support via covalent bonds, and b) optionally replacing one or more of $R_1$ or $R_2$ with any other $R_1$ or $R_2$ respectively.

Preferably, SS is selected from the group consisting of polyolefins, polyacrylates, polymethacrylates, and copolymers thereof.

Also preferably, the supported phosphine compound is of Formula 1A:

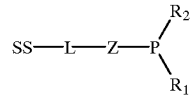

wherein Z is a divalent or trivalent attaching group covalently attached to at least one phosphorus in the phosphine, selected from the group consisting of hydrocarbylene, substituted hydrocarbylene, —O—, —S—, and —NQ—, where Q is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms. Most preferably, SS is polystyrene; L is —CH$_2$—; Z is —(NQ)—; Q is selected from the group consisting of n-propyl, and t-butyl; $R_1$ is selected from the group consisting of bromo, chloro, phenyl, methyl, i-propyl, mesityl, cyclohexyl, 3-methoxyphenyl, and 2-thienyl, —CH$_2$CH(C$_2$H$_5$)CH$_2$O(CH$_2$)$_3$CH$_3$, and —CH$_2$CH(C$_2$H$_5$)CH$_2$OCH$_2$C$_6$H$_5$; and $R_2$ is selected from the group consisting 2-furanyl, 2-(5-methylfuranyl), 2-thienyl, 2,4-dimethoxyphenyl, 2,4,6-trimethoxyphenyl, 2-N,N-dimethyl-5-toluidinyl, 4-pyrrolidino-3-pyridinyl, 2,5-dimethyl-1-N(4'-methylphenyl)pyrrolidinyl, p-[(2,5-dimethyl)-1-pyrrolidinyl]phenyl, and 2,5-dimethoxylphenyl.

The invention is also directed towards supported phosphine compounds of Formula 1:

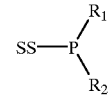

wherein SS is a solid support; $R_1$ is selected from the group consisting of halogen, hydrocarbyl, substituted hydrocarbyl, heterocyclic and substituted heterocyclic; and $R_2$ is selected from the group consisting of cyclic hydrocarbyl, substituted cyclic hydrocarbyl, heterocyclic and substituted heterocyclic.

Preferably, SS is selected from the group consisting of polyolefins, polyacrylates, polymethacrylates, and copolymers thereof.

Also preferably, the supported phosphine compound is of Formula 1A:

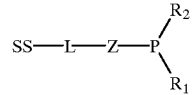

wherein Z is a divalent or trivalent attaching group covalently attached to at least one phosphorus in the phosphine, selected from the group consisting of hydrocarbylene, substituted hydrocarbylene, —O—, —S—, and —NQ—, where Q is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms. Most preferably, SS is polystyrene; L is —CH$_2$—; Z is —(NQ)—; Q is selected from the group consisting of n-propyl, and t-butyl; $R_1$ is selected from the group consisting of bromo, chloro, phenyl, methyl, i-propyl, mesityl, cyclohexyl, 3-methoxyphenyl, and 2-thienyl, —$CH_2CH(C_2H_5)CH_2O(CH_2)_3CH_3$, and —$CH_2CH(C_2H_5)CH_2OCH_2C_6H_5$; and $R_2$ is selected from the group consisting 2-furanyl, 2-(5-methylfuranyl), 2-thienyl, 2,4-dimethoxyphenyl, 2,4,6-trimethoxyphenyl, 2-N,N-dimethyl-5-toluidinyl, 4-pyrrolidino-3-pyridinyl, 2,5-dimethyl-1-N(4'-methylphenyl)pyrrolidinyl, 2,5-dimethyl-1-N-phenylpyrrolidinyl, and 2,5-dimethoxylphenyl.

DETAILED DESCRIPTION OF THE INVENTION

This invention is directed to compositions and processes to prepare polymer-supported phosphine and phosphine oxide compounds and the corresponding free compounds after their cleavage from the polymer support.

More specifically, the invention is directed towards a process to prepare a supported phosphine compound of Formula 1:

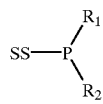

wherein SS is a solid support; $R_1$ is selected from the group consisting of halogen, hydrocarbyl, substituted hydrocarbyl, heterocyclic and substituted heterocyclic; and $R_2$ is selected from the group consisting of halogen, cyclic hydrocarbyl, substituted cyclic hydrocarbyl, heterocyclic and substituted heterocyclic. The process comprises the steps of: a) contacting a phosphine of the formula $XPR_1R_2$, wherein X is a halogen, with the solid support, resulting in the P in the phosphine attached indirectly or directly to the solid support via a covalent bonds, and b) optionally replacing one or more of $R_1$ or $R_2$ with any other $R_1$ or $R_2$.

Preferably, SS is selected from the group consisting of polyolefins, polyacrylates, polymethacrylates, and copolymers thereof.

Also preferably, the supported phosphine compound is of Formula 1A:

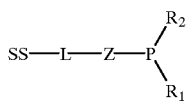

wherein Z is a divalent or trivalent attaching group covalently attached to at least one phosphorus in the phosphine, selected from the group consisting of hydrocarbylene, substituted hydrocarbylene, —O—, —S—, and —NQ—, where Q is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms. Most preferably, SS is polystyrene; L is —$CH_2$—; Z is —(NQ)—; Q is selected from the group consisting of n-propyl, and t-butyl; $R_1$ is selected from the group consisting of bromo, chloro, phenyl, methyl, i-propyl, mesityl, cyclohexyl, 3-methoxyphenyl, and 2-thienyl, —$CH_2CH(C_2H_5)CH_2O(CH_2)_3CH_3$, and —$CH_2CH(C_2H_5)CH_2OCH_2C_6H_5$; and $R_2$ is selected from the group consisting 2-furanyl, 2-(5-methylfuranyl), 2-thienyl, 2,4-dimethoxyphenyl, 2,4,6-trimethoxyphenyl, 2-N,N-dimethyl-5-toluidinyl, 4-pyrrolidino-3-pyridinyl, 2,5-dimethyl-1-N(4'-methylphenyl)pyrrolidinyl, p-[(2,5-dimethyl)-1-pyrrolidinyl]phenyl, and 2,5-dimethoxylphenyl.

The invention is also directed towards supported phosphine compounds of Formula 1:

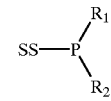

wherein SS is a solid support; $R_1$ is selected from the group consisting of halogen, hydrocarbyl, substituted hydrocarbyl, heterocyclic and substituted heterocyclic; and $R_2$ is selected from the group consisting of cyclic hydrocarbyl, substituted cyclic hydrocarbyl, heterocyclic and substituted heterocyclic.

Preferably, SS is selected from the group consisting of polyolefins, polyacrylates, polymethacrylates, and copolymers thereof.

Also preferably, the supported phosphine compound is of Formula 1A:

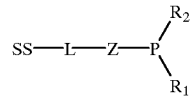

wherein Z is a divalent or trivalent attaching group covalently attached to at least one phosphorus in the phosphine, selected from the group consisting of hydrocarbylene, substituted hydrocarbylene, —O—, —S—, and —NQ—, where Q is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms. Most preferably, SS is polystyrene; L is —$CH_2$—; Z is —(NQ)—; Q is selected from the group consisting of n-propyl, and t-butyl; $R_1$ is selected from the group consisting of bromo, chloro, phenyl, methyl, i-propyl, mesityl, cyclohexyl, 3-methoxyphenyl, and 2-thienyl, —$CH_2CH(C_2H_5)CH_2O(CH_2)_3CH_3$, and —$CH_2CH(C_2H_5)CH_2OCH_2C_6H_5$; and $R_2$ is selected from the group consisting 2-furanyl, 2-(5-methylfuranyl), 2-thienyl, 2,4-dimethoxyphenyl, 2,4,6-trimethoxyphenyl, 2-N,N-dimethyl-5-toluidinyl, 4-pyrrolidino-3-pyridinyl, 2,5-dimethyl-1-N(4'-methylphenyl)pyrrolidinyl, 2,5-dimethyl-1-N-phenylpyrrolidinyl, and 2,5-dimethoxylphenyl.

By hydrocarbyl is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, cyclopentyl, methylcyclopentyl, cyclohexyl, methylcyclohexyl, benzyl, phenyl, o-tolyl, m-tolyl, p-tolyl, xylyl, vinyl, allyl, butenyl, cyclohexenyl, cyclooctenyl, cyclooctadienyl, and butynyl. Examples of substituted hydrocarbyl groups include methoxy, phenoxy, toluyl, chlorobenzyl, fluoroethyl, p-$CH_3$—S—$C_6H_5$, 2-methoxypropyl, and $(CH_3)_3SiCH_2$-.

Virtually any solid material may be used as a support in the context of this invention as long as it meets the following criteria:

The material is insoluble in organic, aqueous, or inorganic solvents. Organic polymer supports are acceptable in this regard but they generally need to be crosslinked. Inorganic support, such as metal oxides ($SiO_2$, $Al_2O_3$, $TiO_2$, $ZrO_2$, etc.), clays, and zeolites, and modified carbons are generally insoluble in these solvents and also may be used as supports.

The support contains reactive sites, which can be used for the covalent attachment of the phosphorus.

The reactive sites are isolated to prevent additional crosslinking during further chemical transformations.

The reactive sites are exposed to the reaction medium. With a polymer resin support this is achieved through the use of a resin which swells in a reaction solvent or is sufficiently porous to allow transport of the reaction medium through the polymer matrix.

The term "solid support" refers to a material having a rigid or semi-rigid surface that contains or can be derivatized to contain functionality, which covalently links a compound to the surface thereof. Other modifications may be made in order to achieve desired physical properties. Such materials are well known in the art and include, by way of example, polystyrene supports, polyacrylamide supports, polyethyleneglycol supports, metal oxides such as silica, and the like. Such supports will preferably take the form of small beads, pellets, disks, films, or other conventional forms, although other forms may be used.

A preferred solid support is an organic or inorganic polymer, to which the phosphorus can be covalently attached through a side chain or pendant group of the polymeric backbone. The polymer may be crosslinked or modified. Suitable preferred polymers useful in the preparation of a supported phosphine compound or a combinatorial library of supported phosphine compounds include polyolefins, polyacrylates, polymethacrylates, and copolymers thereof that meet the general criteria described above. A more preferred polymeric support is polystyrene wherein the phosphorus is attached to a pendant phenyl group on the polystyrene backbone. Most preferred is polystyrene, crosslinked with divinylbenzene. Specifically, polystyrenes commonly used for solid phase synthesis have been used. These particular resins are crosslinked with from 1 to 10 wt % divinylbenzene. The styrene moieties are substituted in the para or meta positions. Only a portion of the styrene moieties are substituted, typically resulting in functional group loadings of approximately 0.2 to 2.0 mmole per gram of resin, although this value may be higher or lower.

Any reaction in which the phosphorus is covalently attached to the solid support may be used to prepare the compounds represented by Formula 1 and 1A, such as those described in *Encyclopedia of Inorganic Chemistry*, John Wiley & Sons, Vol. 6, pg. 3149–3213, herein incorporated by reference.

One embodiment of attaching the P to the solid support is via the reaction of the halogen or hydrogen bonded to the phosphorus in the phosphine with a nucleophilic group that is covalently attached to a solid support. The term nucleophilic group is a term well recognized in the art and refers to chemical moieties having a reactive pair of electrons. This scheme can easily be adapted for combinatorial synthesis.

Any of the substituents in the above compounds may be replaced by other functional groups using any procedure known in the art. One or all of the substituents can be reacted in a single reaction, depending on the choice of reactants and reaction conditions. These reactions can easily be adapted for combinatorial processes. These procedures and other procedures to prepare the compounds represented by Formula 1 and 1A are detailed in U.S. patent application Ser. No. 09/415,347, filed Oct. 8, 1999, herein fully incorporated by reference.

Any of the substituents in the above compounds may be replaced by other functional groups using any procedure known in the art. One or all of the substituents can be reacted in a single reaction, depending on the choice of reactants and reaction conditions.

The processes of the instant invention can easily be adapted for combinatorial processes and to create combinatorial libraries of the compounds of the instant invention. Additionally, the process of the instant invention can be used to prepare chiral phosphine compounds, without any loss of chirality present in the starting materials.

As used herein, a combinatorial library is an intentionally created collection of a plurality of differing molecules which can be prepared by selected synthetic means and screened for a desired activity or characteristic in a variety of formats (e.g., libraries of soluble molecules, libraries of compounds attached to resin beads, silica chips, or other solid supports). The libraries are generally prepared such that the compounds are in approximately equimolar quantities, and are prepared by combinatorial synthesis. Combinatorial synthesis refers to the parallel synthesis of diverse compounds by sequential additions of multiple choices of reagents which leads to the generation of large chemical libraries containing related molecules having molecular diversity. Screening methods for libraries vary greatly and are dependent upon a desired activity, the size of library, and the class of compounds in the library.

The libraries of the instant invention can be of any type. These types include but are not limited to arrays and mixtures. Arrays are libraries in which the individual compounds are simultaneously synthesized in spatially segregated locations, typically identified by their location on a grid. Mixture libraries contain a mixture of compounds that are simultaneously synthesized and assayed. Identification of the most active compound is then performed by any of several techniques well known in the combinatorial art, such as deconvolution (*Proc. Natl. Acad. Sci. USA*, 91, pg. 10779 (1994)).

A preferred solid support for the combinatorial libraries of the instant invention is an organic or inorganic polymer as described above, to which the phosphorus can be covalently attached through a side chain or pendant group of the polymeric backbone.

The invention is also directed to a process to prepare a phosphine compound selected from the group consisting of Formula 2 and 3:

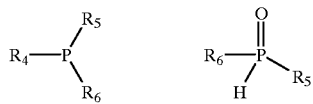

wherein $R_4$ is a halogen; $R_5$ is selected from the group consisting of halogen, hydrocarbyl, substituted hydrocarbyl, heterocyclic and substituted heterocyclic; and R$_6$ is selected from the group consisting of cyclic hydrocarbyl, substituted cyclic hydrocarbyl, heterocyclic and substituted heterocyclic; comprising the steps of: contacting a supported phosphine compound of the Formula 1:

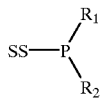

wherein SS is a solid support; R$_1$ is selected from the group consisting of halogen, hydrocarbyl, substituted hydrocarbyl, heterocyclic and substituted heterocyclic; and R$_2$ is selected from the group consisting of cyclic hydrocarbyl, substituted cyclic hydrocarbyl, heterocyclic and substituted heterocyclic with an compound of the Formula ER$_9$, wherein E is an electrophilic group and R$_9$ is selected from the group consisting of halogen, hydrocarbyl, substituted hydrocarbyl, heterocyclic and substituted heterocyclic; thereby forming the corresponding compound of Formula 1 and 2; and optionally replacing one or more of R$_4$, R$_5$, and R$_6$ with any R$_4$, R$_5$, and R$_6$.

Preferably the supported phosphine compound is of Formula 1A:

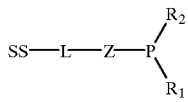

wherein Z is a divalent or trivalent attaching group covalently attached to at least one phosphorus in the phosphine, selected from the group consisting of hydrocarbylene, substituted hydrocarbylene, —O—, —S—, and —NQ—, where Q is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms Also preferably ER$_9$ is selected from the group consisting of PCl$_3$ and water. More preferably, L is —CH$_2$—; Z is —(NQ)—; Q is selected from the group consisting of n-propyl, and t-butyl; R$_4$ is chloro; R$_5$ is selected from the group consisting of bromo, chloro, methyl, i-propyl, phenyl, —CH$_2$CH(C$_2$H$_5$)CH$_2$O(CH$_2$)$_3$CH$_3$, and —CH$_2$CH(C$_2$H$_5$)CH$_2$OCH$_2$C$_6$H$_5$; and R$_6$ is selected from the group consisting of phenyl, 2-N,N-dimethyl-5-toluidinyl, 2-[(2,5-dimethyl)-1-pyrrolidinyl]-4-methylphenyl, 2,4-dimethoxyphenyl, and 2,5-dimethoxylphenyl.

In the above process, E is any electrophilic group that will cleave the covalent bond attaching the phosphorus to the solid support. The term electrophilic group is a term well recognized in the art and refers to chemical moieties, which can accept a pair of electrons from a nucleophilic group as defined above. Suitable electrophilic groups include trimethylsilyl, PCl$_2$, halogens, and protons donated from compounds such as acids, water, alcohols, or amines.

In the instance where ER$_9$ is water, the resulting POH group would rearrange to yield to form the compounds of Formula 3. These compounds can also be formed from any other of Formula 2 via the replacement of one or more of R$_4$, R$_5$, and R$_6$ with an —OH group using any method known in the art. An equivalent rearrangement occurs when a PSH group is present.

Any of the substituents in the above compounds may be replaced by other functional groups. One or all of the substituents can be reacted in a single reaction, depending on the choice of reactants and reaction conditions. These reactions can easily be adapted for combinatorial processes. These procedures and other procedures to prepare the compounds represented by Formula 1 and 1A are detailed in U.S. patent application Ser. No. 09/415,347, filed Oct. 8, 1999, herein fully incorporated by reference.

The processes of the instant invention can easily be adapted for combinatorial processes and to create combinatorial libraries of the compounds of the instant invention. Additionally, the process of the instant invention can be used to prepare chiral phosphine compounds, without any loss of chirality present in the starting materials. To create a library, one or more supported phosphines are reacted with one or more compounds of the Formula ER$_9$, generating a plurality of phosphine compounds.

The processes of the instant invention are preferably performed under dry, inert atmosphere with dry, deoxygenated solvents. Any solvent is suitable provided that it is inert to all reagents and products. Optimum temperatures are about −80 to about 200° C., preferably about −80 to about 150° C.

The phosphorus compounds and libraries described herein, both supported and unsupported, can be utilized as ligands for catalytic compounds. The compounds can be complexed with one or more transition metals to form a coordination compound.

"Coordination compound" refers to a compound formed by the union of a metal ion (usually a transition metal) with a non-metallic ion or molecule called a ligand or complexing agent.

The transition metals are hereby defined as metals of atomic number 21 through 83. Preferably, the transition metal is from Periodic Group VIII, hereby defined as Fe, Co, Ni, Ru, Rh, Pd, Os, Ir, and Pt. Preferred is Pd. The complex can be made by any synthetic method known in the art, either through direct reaction or via the use of a transition metal precursor. Many of these techniques are described in Hartley, "*Chem. Met.-Carbon Bond*", Hartley, F. R (Ed), 1987, vol. 4, pp. 1163–1225.

One reaction in which the compounds of the instant invention can be utilized as catalysts is in the cross-coupling of aryl halides with thiols. This type of reaction is described in Zheng, et al., *J. Org. Chem.*, 63, p9606–9607, 1998.

The following non-limiting Examples are meant to illustrate the invention but are not intended to limit it in any way.

Materials and Methods

All manipulations of air-sensitive materials were carried out with rigorous exclusion of oxygen and moisture in Schlenk-type glassware on a dual manifold Schlenk line, interfaced to a high-vacuum (10$^{-4}$–10$^{-5}$ Torr) line, or in a nitrogen-filled Vacuum Atmospheres glovebox with a high-capacity recirculator (1–2 ppm of O$_2$). Before use, all solvents were distilled under dry nitrogen over appropriate drying agents (sodium benzophenone ketyl, metal hydrides except for chlorinated solvents). THF-$D_8C_6D_6$ and $CDCl_3$ were purchased from Cambridge Isotopes (Andover, Mass.). All organic and inorganic starting materials were purchased from Aldrich Chemical Co. (Milwaukee Wis.), Farchan Laboratories Inc. (Gainesville, Fla.), Strem Chemicals (Newburyport, Mass.), Calbiochem-NovaBiochem Corp. (San Diego, Calif.), Rieke Metals, Inc. (Lincoln, Nebr.), or Lancaster Synthesis Inc. (Windham, N.H.), and when appropriate were distilled prior to use.

Physical and Analytical Measurements

NMR spectra were recorded on either a Nicolet NMC-300 wide-bore (FT, 300 MHz, $^1H$; 75 MHz, $^{13}C$, 121 MHz $^{31}P$), or GE QM-300 narrow-bore (FT, 300 MHz, $^1H$) instrument. Chemical shifts (δ) for $^1H$, $^{13}C$ are referenced to internal solvent resonances and reported relative to $SiMe_4$. $^{31}P$ NMR shifts are reported relative to external phosphoric acid. Analytical gas chromatography was performed on a Varian Model 3700 gas chromatograph with FID detectors and a Hewlett-Packard 3390A digital recorder/integrator using a 0.125 in. i.d. column with 3.8% w/w SE-30 liquid phase on Chromosorb W support. GC/MS studies were conducted on a VG 70-250 SE instrument with 70 eV electron impact ionization.

EXAMPLES

Synthesis of Polymer-Supported P—C—X (X=O, S) Ligands

Example 1

Polymer-Bound 2-P(Br)$C_4H_3O$

A solution of $CH_3CH_2CH_2NH_2$ (224 g, 3.8 moles) and KI (0.3 g, 2 mmol) in 1000 mL of THF was treated with chloromethylpolystyrene-divinylbenzene (Merrified resin, 2% DVB, 100 g, 1.10 mmol/g, 110 mmol) while stirring at room temperature for 30 min. The suspension was then refluxed for 24 hours before the solution was filtered off. The resulting resin was washed with $H_2O$ (3×250 mL), THF (3×150 mL), hexane (3×200 mL). After drying in vacuum overnight, ca. 100 g of the resin were obtained. The disappearance of $^1H$ resonances of polymer-Ph—$CH_2$—Cl ($CH_2$= ~4.5 ppm) indicates that the complete transformation of the chloromethyl groups to n-propylaminomethyl groups.

A solution of $PBr_3$ (25.0 g, 92.4 mm) and furan (7.0 g, 102.8 mm) in 150 mL of pyridine was refluxed for 5 h. to give the crude 2-furyldibromo-phosphine ($^{31}P$ NMR: δ103.5 ppm). This compound was used directly for the next step without further purification. Next, polymer-supported n-propylamine (10.0 g, 1.1 mmol/g, 11.0 mmol) was slowly added into the mixture above while stirring at room temperature for a period of 10 min. The resulting suspension was stirred at room temperature overnight before the solution was filtered off. The resin was washed with THF (2×50 mL), hexane (3×50 mL), $CH_2Cl_2$ (4×50 mL), and hexane (2×50 mL). The resulting resin was dried in vacuum overnight to yield the polymer-supported P(Br)$C_4H_3O$. $^{31}P$ NMR (122 MHz, $CDCl_3$): δ113.1 ppm.

Example 2

Polymer-Bound 2-P(Br)-5-(Me)$C_4H_2O$

The polymer-supported amine was prepared as in Example 1 using $(CH_3)_3C$—$NH_2$ in place of the n-propylamine. A solution of $PBr_3$ (20.0 g, 73.9 mm) and 2-methylfuran (6.6 g, 80.4 mm) in 150 mL of pyridine was stirred at room temperature for 15 h to give the crude 2-methylfuryl-5-dibromophosphine ($^{31}P$ NMR: δ102.1 ppm). This compound was used directly for the next step without further purification. Next, polymer-supported t-butylamine (10.0 g, 1.1 mmol/g, 11.0 mmol) was slowly added into the mixture above while stirring at room temperature for a period of 10 min. The resulting suspension was stirred at room temperature overnight before the solution was filtered off. The resin was washed with THF (2×50 mL), hexane (3×50 mL), $CH_2Cl_2$ (4×50 mL), and hexane (2×50 mL). The resulting resin was dried in vacuum overnight to yield the polymer-supported 2-P(Br)-5-(Me)$C_4H_2O$. $^{31}P$ NMR (122 MHz, $CDCl_3$): δ109.3 ppm.

Example 3

Polymer-Bound 2-P(Br)$C_4H_3S$

A solution of $PBr_3$ (5.5 g, 20.3 mm) and thiophene (2.0 g, 23.8 mm) in 50 mL of pyridine was refluxed for 3 days to give the crude 2-thienyldibromo-phosphine ($^{31}P$ NMR: δ132.7 ppm). This compound was used directly for the next step without further purification. Next, polymer-supported n-propylamine prepared as in Example 1 (3.0 g, 1.1 mmol/g, 3.3 mmol) was slowly added into the mixture above while stirring at room temperature for a period of 10 min. The resulting suspension was stirred at room temperature overnight before the solution was filtered off. The resin was washed with THF (2×50 mL), hexane (3×30 mL), $CH_2Cl_2$ (4×50 mL), and hexane (2×50 mL). The resulting resin was dried in vacuum overnight to yield the polymer-supported 2-P(Br)$C_4H_3S$. $^{31}P$ NMR (122 MHz, $CDCl_3$): δ126.9 ppm.

Example 4

Polymer-Bound P($C_4H_3O$)($C_4H_3S$)

A suspension of polymer-bound P(Br)$C_4H_3O$ from Example 1 (1.0 g, 0.913 mmol, 0.913 mm/g), and 2-$C_4H_3$SLi (11.0 mmol, 1.0 M in THF solution) in 10 mL of THF was stirred at room temperature over 2 h before the solution was filtered off. The resulting resin was washed with THF (2×50 mL), $CH_2Cl_2$ (3×10 mL), $Me_2CHOH$ (2×50 mL), THF/$H_2O$ (70/30 volume ratio, 2×50 mL) and hexane (3×50 mL). The resin was dried in vacuum overnight. $^{31}P$ NMR (122 MHz, $CDCl_3$): δ28.4 ppm.

The results from the synthesis of polymer-supported P—C—O and P—C—S ligands are summarized below in Table 1.

TABLE 1

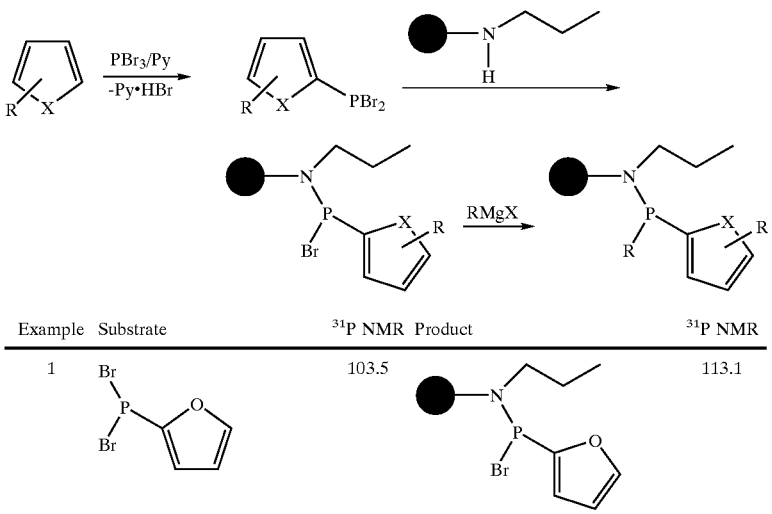

| Example | Substrate | 31P NMR | Product | 31P NMR |
|---|---|---|---|---|
| 1 | 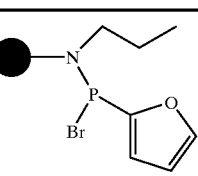 | 103.5 | 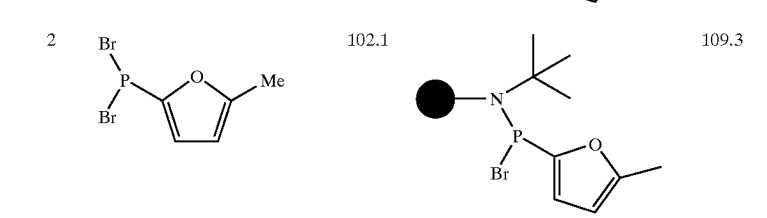 | 113.1 |
| 2 | 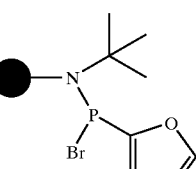 | 102.1 | 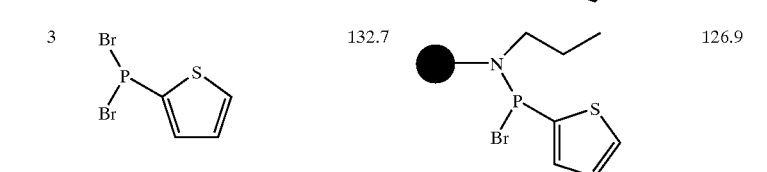 | 109.3 |
| 3 | 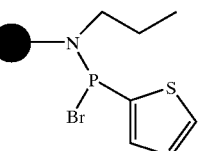 | 132.7 | 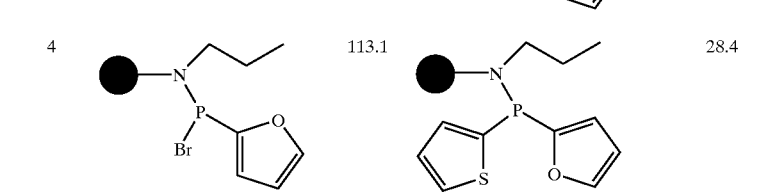 | 126.9 |
| 4 | 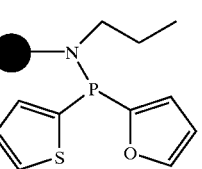 | 113.1 | | 28.4 |

Synthesis of Polymer-Supported P—$C_2$—N Ligands

Example 5

Polymer-Bound 2-P(Br)-1-$NMe_2$-4-(Me)$C_6H_3$

A solution of $PBr_3$ (7.0 g, 26.0 mm) in 80 mL of pyridine was treated with N,N-dimethyl-p-toluidine (10.0 g, 74.0 mm) over a period of 5 min. The resulting mixture was then refluxed overnight. to give the crude 2-dibromophosphino-N,N-dimethyl-p-toluidine ($^{31}$P NMR: δ149.1 ppm). This compound was used directly for the next step without further purification. Next, polymer-supported secondary amines prepared as in Example 1 (10.0 g, 1.06 mmol/g, 10.6 mmol) was slowly added into the mixture above while stirring at room temperature for a period of 10 min. The resulting suspension was stirred at room temperature overnight before the solution was filtered off. The resin was washed with THF (2×50 mL), hexane (3×50 mL), $CH_2Cl_2$ (4×50 mL), and hexane (2×50 mL). The resulting resin was dried in vacuum overnight to yield the polymer-supported 2-P(Br)-1-$NMe_2$-4-(Me)$C_6H_3$ $^{31}$P NMR (122 MHz, $CDCl_3$): δ157.0 ppm.

Example 6

Polymer-Bound 2-P(Me)-1-$NMe_2$-4-(Me)$C_6H^3$

A suspension of polymer-bound 2-P(Br)-1-$NMe_2$-4-$MeC_6H_3$ (1.0 g, 0.84 mmol, 0.84 mm/g) from Example 5, and MeMgCl (12.0 mmol, 1.0 M in THF solution) in 10 mL of THF was stirred at room temperature over night before the solution was filtered off. The resulting resin was washed with THF (3×20 mL), $CH_2Cl_2$ (3×10 mL), $Me_2CHOH$ (2×10 mL), THF/$H_2O$ (70/30 volume ratio, 2×20 mL) and hexane (3×10 mL). The resin was dried in vacuum overnight. $^{31}$P NMR (122 MHz, $CDCl_3$): δ48.5 ppm.

Example 7

Polymer-Bound 2-P(Ph)-1-$NMe_2$-4-(Me)$C_6H_3$

A suspension of polymer-bound 2-P(Br)-1-$NMe_2$-4-$MeC_6H_3$ (1.0 g, 0.84 mmol, 0.84 mm/g) from Example 5, and PhMgCl (12.0 mmol, 1.0 M in THF solution) in 10 mL of THF was stirred at room temperature over night before the solution was filtered off. The resulting resin was washed with THF (3×20 mL), CH$_2$Cl$_2$ (3×10 mL), Me$_2$CHOH (2×10 mL), THF/H$_2$O (70/30 volume ratio, 2×20 mL) and hexane (3×10 mL). The resin was dried in vacuum overnight. $^{31}$P NMR (122 MHz, CDCl$_3$): δ60.4 ppm.

Example 8

Polymer-Bound 2-P(3-MeC$_6$H$_4$)-1-NMe$_2$-4-(Me)C$_6$H$_3$

A suspension of polymer-bound 2-P(Br)-1-NMe$_2$-4-MeC$_6$H$_3$ (1.0 g, 0.84 mmol, 0.84 mm/g) from Example 5, and 3-MeC$_6$H$_4$MgCl (12.0 mmol, 1.0 M in THF solution) in 10 mL of THF was stirred at room temperature over night before the solution was filtered off. The resulting resin was washed with THF (3×20 mL), CH$_2$Cl$_2$ (3×10 mL), Me$_2$CHOH (2×10 mL), THF/H$_2$O (70/30 volume ratio, 2×20 mL) and hexane (3×10 mL). The resin was dried in vacuum overnight. $^{31}$P NMR (122 MHz, CDCl$_3$): δ60.5 ppm.

Example 9

Polymer-Bound 2-P(2-(MeO)C$_6$H$_4$)-1-NMe$_2$-4-(Me)C$_6$H$_3$

A suspension of polymer-bound 2-P(Br)-1-NMe$_2$-4-(Me)C$_6$H$_3$ (1.0 g, 0.84 mmol, 0.84 mm/g) from Example 5, and 2-(MeO)C$_6$H$_4$MgBr (12.0 mmol, 1.0 M in THF solution) in 10 mL of THF was stirred at room temperature over night before the solution was filtered off. The resulting resin was washed with THF (3×20 mL), CH$_2$Cl$_2$ (3×10 mL), Me$_2$CHOH (2×10 mL), THF/H$_2$O (70/30 volume ratio, 2×20 mL) and hexane (3×10 mL). The resin was dried in vacuum overnight. $^{31}$P NMR (122 MHz, CDCl$_3$): δ51.0 ppm.

Example 10

Polymer-Bound 2-P(2-C$_4$H$_3$S)-1-NMe$_2$-4-(Me)C$_6$H$_3$

A suspension of polymer-bound 2-P(Br)-1-NMe$_2$-4-MeC$_6$H$_3$ (1.0 g, 0.84 mmol, 0.84 mm/g) from Example 5, and 2-C$_4$H$_3$SLi (12.0 mmol, 1.0 M in THF solution) in 10 mL of THF was stirred at room temperature overnight before the solution was filtered off. The resulting resin was washed with THF (3×20 mL), CH$_2$Cl$_2$ (3×10 mL), Me$_2$CHOH (2×10 mL), THF/H$_2$O (70/30 volume ratio, 2×20 mL) and hexane (3×10 mL). The resin was dried in vacuum overnight. $^{31}$P NMR (122 MHz, CDCl$_3$): δ44.6 ppm.

The results from Examples 5–10 are summarized below in Table 2.

TABLE 2

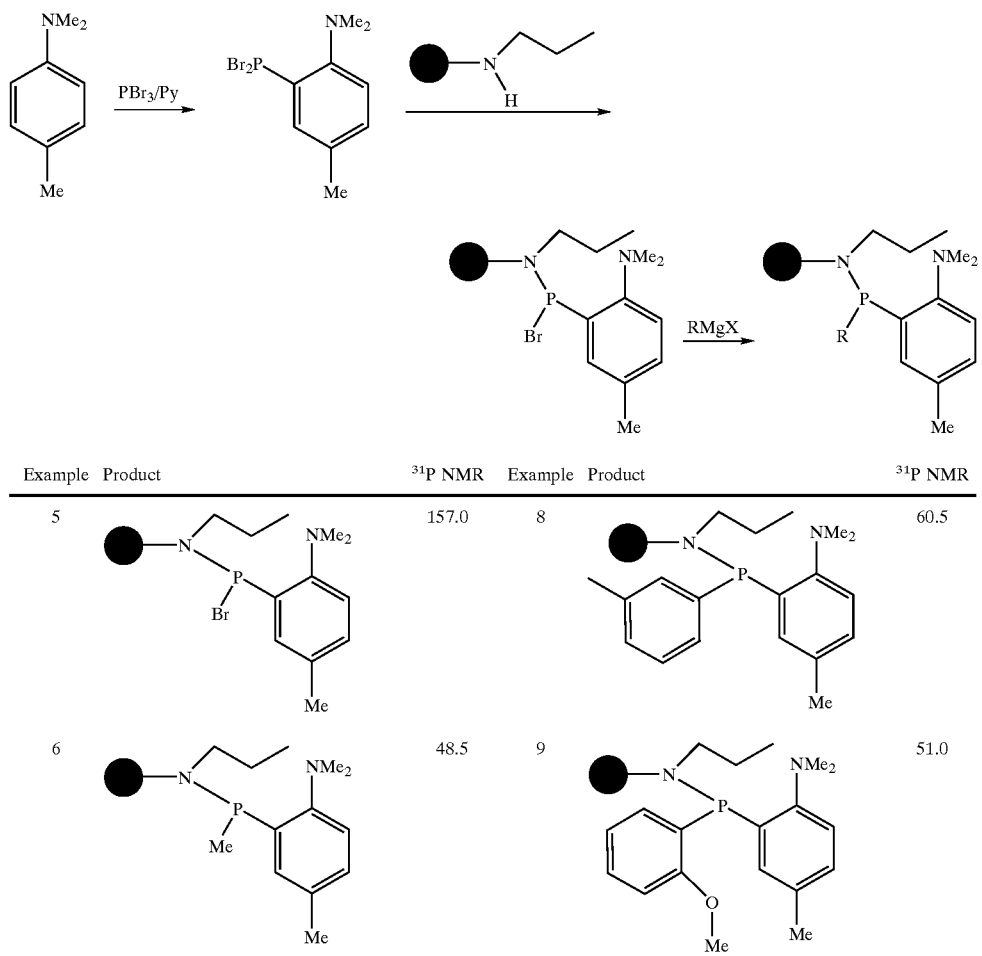

TABLE 2-continued

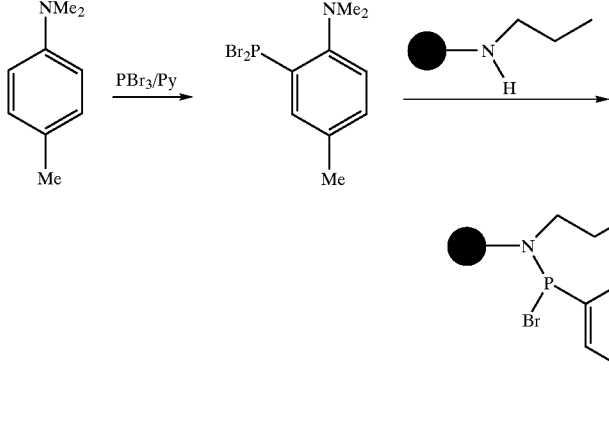

| Example | Product | $^{31}$P NMR | Example | Product | $^{31}$P NMR |
|---|---|---|---|---|---|
| 7 | 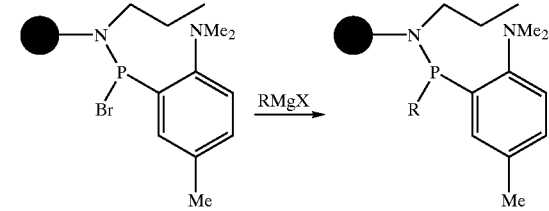 | 60.4 | 10 | 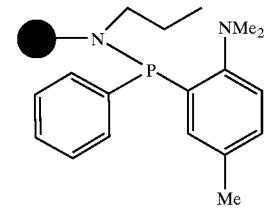 | 44.6 |

Example 11

Polymer-Bound 3-P(Br)-4-(NC$_4$H$_8$)C$_5$H$_3$N

A solution of PBr$_3$ (8.8 g, 32.5 mm) in 100 mL of pyridine was treated with 4-pyrrolidinopyridine (5.0 g, 33.7 mm) over a period of 5 min. The resulting mixture was then stirred at room temperature for 3 days to give the crude 3-dibromophosphino-4-pyrrolidinopyridine ($^{31}$P NMR: δ152.2 ppm). This compound was used directly for the next step without further purification. Next, polymer-supported secondary amines from Example 1 (9.0 g, 1.1 mmol/g, 9.9 mmol) was slowly added into the mixture above while stirring at room temperature for a period of 10 min. The resulting suspension was refluxed overnight before the solution was filtered off. The resin was washed with THF (2×50 mL), hexane (3×50 mL), CH$_2$Cl$_2$ (4×50 mL), and hexane (2×50 mL). The resulting resin was dried in vacuum overnight to yield the polymer-supported 3-P(Br)-4-(NC$_4$H$_8$)C$_5$H$_3$N. $^{31}$P NMR (202 MHz, CDCl$_3$): δ168.4 ppm.

Example 12

Polymer-Bound 3-P(Ph)-4-(NC$_4$H$_8$)C$_5$H$_3$N

A suspension of polymer-bound 3-P(Br)-4-(NC$_4$H$_8$)C$_5$H$_3$N (10.0 g, 8.98 mmol, 0.898 mm/g) from Example 11, and PhMgBr (100.0 mmol, 1.0 M in THF solution) in 100 mL of THF was refluxed over night before the solution was filtered off. The resulting resin was washed with THF (3×50 mL), CH$_2$Cl$_2$ (3×50 mL), Me$_2$CHOH (2×30 mL), THF/H$_2$O (70/30 volume ratio, 2×50 mL) and hexane (3×40 mL). The resin was dried in vacuum overnight. $^{31}$P NMR (122 MHz, CDCl$_3$): δ67.8 ppm.

Example 13

Polymer-Bound 3-P(Me$_3$C$_6$H$_2$)-4-(NC$_4$H$_8$)C$_5$H$_3$N

A suspension of polymer-bound 3-P(Br)-4(NC$_4$H$_8$)C$_5$H$_3$N (7.0 g, 6.29 mmol, 0.898 mm/g) from Example 11, and 2,4,6-Me$_3$C$_6$H$_2$MgBr (100.0 mmol, 1.0 M in THF solution) in 100 mL of THF was refluxed over night before the solution was filtered off. The resulting resin was washed with THF (3×50 mL), CH$_2$Cl$_2$ (3×50 mL), Me$_2$CHOH (2×30 mL), THF/H$_2$O (70/30 volume ratio, 2×50 mL) and hexane (3×40 mL). The resin was dried in vacuum overnight. $^{31}$P NMR (122 MHz, CDCl$_3$): δ46.1 ppm.

Example 14

Polymer-Bound (+/−)-2,5-Me$_2$—C$_4$H$_6$-1-N(2'-PCl-4'-Me)C$_6$H$_3$

A solution of PCl$_3$ (36.3 g, 264.3 mm) in 200 mL of pyridine was treated with (+/−)-2,5-dimethyl-1-N(4'-methylphenyl)pyrrolidine (10.0 g, 52.8 mm) over a period of 5 min. The resulting mixture was then refluxed for 2 days to give the crude (+/−)-2,5-dimethyl-1-N(2'-dichlorophosphino-4'-methylphenyl)pyrrolidine ($^{31}$P NMR: δ164.7 (s), 159.9 (s) ppm). After precipitates (Py.HCl) were filtered off, the excess PCl$_3$ and pyridine solvent were removed from filtrates, a mixture of 100 mL of pyridine and 300 mL of THF was added to the resulting residue. Next, polymer-supported secondary amines (15.0 g, 1.1 mmol/g, 16.5 mmol) was slowly added into the mixture above while stirring at room temperature for a period of 10 min. The resulting suspension was refluxed overnight before the solution was filtered off. The resin was washed with THF (2×50 mL), hexane (3×50 mL), CH$_2$Cl$_2$ (4×50 mL), and hexane (2×50 mL). The resulting resin was dried in vacuum overnight to yield the polymer-supported (+/−)-2,5-dimethyl-1-N(1-N(2'-chlorophosphino-4'-methylphenyl)pyrrolidine. $^{31}$P NMR (122 MHz, CDCl$_3$): δ145.1, 136.0 ppm.

Example 15

Polymer-Bound (+/−)-2,5-Me$_2$—C$_4$H$_6$-1-N(2'-PPh-4'-Me)C$_6$H$_3$

A suspension of polymer-bound (+/−)-2,5-Me$_2$—C$_4$H$_6$-1-N(2'-PCl-4'-Me) C$_6$H$_3$ (2.0 g, 1.804 mmol, 0.902 mm/g)

from Example 14, and PhMgCl (24.0 mmol, 2.0 M in THF solution) in 20 mL of THF was refluxed overnight before the solution was filtered off. The resulting resin was washed with THF (3×10 mL), CH$_2$Cl$_2$ (3×10 mL), Me$_2$CHOH (2×10 mL), THF/H$_2$O (70/30 volume ratio, 2×20 mL) and hexane (3×10 mL). The resin was dried in vacuum overnight. $^{31}$P NMR (122 MHz, CDCl$_3$): δ63.4, 57.2 ppm.

Example 16

Polymer-Bound (+/−)-2,5-Me$_2$—C$_4$H$_6$-1-N(2'-PMe-4'-Me)C$_6$H$_3$

A suspension of polymer-bound (+/−)-2,5-Me$_2$—C$_4$H$_6$-1-N(2'-PCl-4'-Me) C$_6$H$_3$ (2.0 g, 1.804 mmol, 0.902 mm/g)

from Example 14, and MeMgCl (24.0 mmol, 2.0 M in THF solution) in 20 mL of THF was refluxed over night before the solution was filtered off. The resulting resin was washed with THF (3×10 mL), CH$_2$Cl$_2$ (3×10 mL), Me$_2$CHOH (2×10 mL), THF/H$_2$O (70/30 volume ratio, 2×20 mL) and hexane (3×10 mL). The resin was dried in vacuum overnight. $^{31}$P NMR (122 MHz, CDCl$_3$): δ26.5, 16.2 ppm.

The results from Examples 11–16 are summarized below in Table 3.

TABLE 3

| Example | Substrate | $^{31}$P NMR | Product | $^{31}$P NMR |
|---|---|---|---|---|
| 11 | | 152.2 | | 168.4 |
| 12 | | 168.4 | | 67.8 |
| 13 | | 168.4 | | 46.1 |
| 14 | | 164.7 159.5 | | 145.1 136.0 |
| 15 | | 145.1 136.0 | | 57.2 63.4 |

TABLE 3-continued

| Example | Substrate | ³¹P NMR | Product | ³¹P NMR |
|---|---|---|---|---|
| 16 | [structure: polymer-N(propyl-tolyl)-P(Cl) with pyrrolidine, (+/-)] | 145.1<br>136.0 | [structure: polymer-N(propyl-tolyl)-P(Me) with pyrrolidine, (+/-)] | 26.5<br>16.2 |

Example 17

Polymer-Bound Chiral (S, S)-2,5-Me$_2$—C$_4$H$_6$-1-N(2'-PCl-4'-Me)C$_6$H$_3$

A solution of PCl$_3$ (9.1 g, 66.3 mm) in 15 mL of pyridine was treated with (S, S)-2,5-dimethyl-1-N(4'-methylphenyl)pyrrolidine (1.03 g, 6.87 mm) over a period of 5 min. The resulting mixture was then refluxed for 2 days to give the crude (S, S)-2,5-dimethyl-1-N(2'-dichlorophosphino-4'-methylphenyl)pyrrolidine (³¹P NMR: δ159.5(s) ppm). After precipitates (Py. HCl) were filtered off, the excess PCl$_3$ and pyridine solvent were removed from filtrates, a mixture of 10 mL of pyridine and 20 mL of THF was added to the resulting residue. Next, polymer-supported secondary amines from Example 1 (2.8 g, 1.1 mmol/g, 3.08 mmol) was slowly added into the mixture above while stirring at room temperature for a period of 10 min. The resulting suspension was refluxed overnight before the solution was filtered off. The resin was washed with THF (2×10 mL), hexane (3×10 mL), CH$_2$Cl$_2$ (4×10 mL), and hexane (2×10 mL). The resulting resin was dried in vacuum overnight to yield the polymer-supported (S, S)-2,5-dimethyl-1-N(2'-chlorophosphino-4'-methylphenyl) pyrrolidine. ³¹P NMR (122 MHz, CDCl$_3$): δ136.0 ppm.

Example 18

Polymer-Bound Chiral (S, S)-2,5-Me$_2$—C$_4$H$_6$-1-N(4'-PCl)C$_6$H$_4$

A solution of PCl$_3$ (5.0 g, 36.4 mm) in 15 mL of pyridine was treated with (S, S)-2,5-dimethyl-1-N-phenylpyrrolidine (0.5 g, 2.87 mm) over a period of 5 min. The resulting mixture was then refluxed for 2 days to give the crude (S, S)-2,5-dimethyl-1-N(4'-dichlorophosphinophenyl)pyrrolidine (³¹P NMR: δ165.8 (s) ppm). After precipitates (Py. HCl) were filtered off, the excess PCl$_3$ and pyridine solvent were removed from filtrates, a mixture of 10 mL of pyridine and 20 mL of THF was added to the resulting residue. Next, polymer-supported secondary amines from Example 1 (2.0 g, 1.1 mmol/g, 2.2 mmol) was slowly added into the mixture above while stirring at room temperature for a period of 10 min. The resulting suspension was stirred at room temperature overnight before the solution was filtered off. The resin was washed with THF (2×10 mL), hexane (3×10 mL), CH$_2$Cl$_2$ (4×10 mL), and hexane (2×10 mL). The resulting resin was dried in vacuum overnight to yield the polymer-supported (S,S)-2,5-dimethyl-1-N(4'-chlorophosphinophenyl)pyrrolidine. ³¹P NMR (122 MHz, CDCl$_3$): δ147.6 ppm.

Example 19

Polymer-Bound Chiral (S, S)-2,5-Me$_2$—C$_4$H$_6$-1-N(4'-PPh)C$_6$H$_4$

A suspension of polymer-bound chiral (S, S)-2,5-Me$_2$—C$_4$H$_6$-1-N(4'-PCl) C$_6$H$_4$ (1.0 g, 0.913 mmol, 0.913 mm/g) from Example 18, and PhMgCl (20.0 mmol, 2.0 M in THF solution) in 10 mL of THF was stirred at room temperature over night before the solution was filtered off. The resulting resin was washed with THF (3×10 mL), CH$_2$Cl$_2$ (3×10 mL), Me$_2$CHOH (2×10 mL), THF/H$_2$O (70/30 volume ratio, 2×10 mL) and hexane (3×10 mL). The resin was dried in vacuum overnight. ³¹P NMR (202 MHz, CDCl$_3$): δ35.6 ppm.

The results from Examples 17–19 are shown below in Table 4.

TABLE 4

Polymer-Supported Synthetic Results of Chiral PN Ligands

| Example | Substrate | ³¹P NMR | Product | ³¹P NMR |
|---|---|---|---|---|
| 17 | [structure: (S,S)-2,5-dimethylpyrrolidine-N-(4-methylphenyl)] | | [structure: (S,S)-2,5-dimethylpyrrolidine-N-(2-PCl$_2$-4-methylphenyl)] | 159.5 |

TABLE 4-continued

Polymer-Supported Synthetic Results of Chiral PN Ligands

| Example | Substrate | | ³¹P NMR | Product | | ³¹P NMR |
|---|---|---|---|---|---|---|
| 18 | 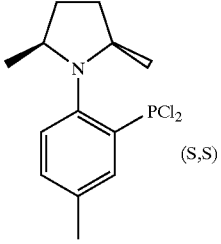 (S,S) | 159.5 | 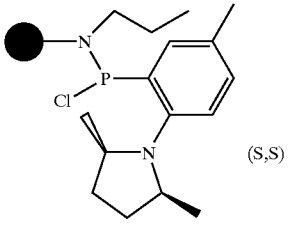 (S,S) | 136.0 |
| | 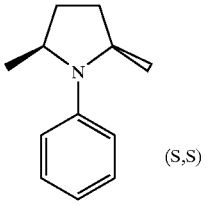 (S,S) | | 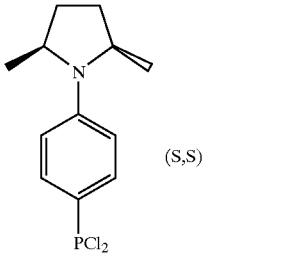 (S,S) | 165.8 |
| 19 | 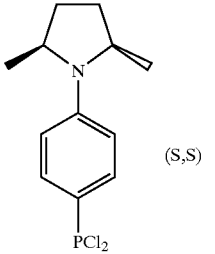 (S,S) | 165.8 | 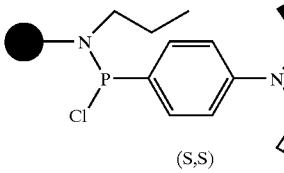 (S,S) | 147.6 |
| | 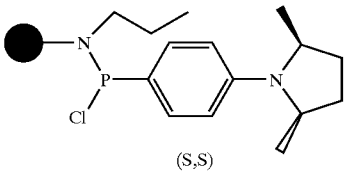 (S,S) | 147.6 | 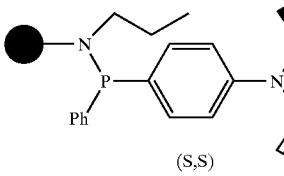 (S,S) | 35.8 |

Synthesis of Polymer-Supported P—C₂—O Ligands

Example 20

Polymer-Bound 2-P(Br)-1,5-(MeO)₂C₆H₃

A solution of PBr₃ (2.5 g, 9.2 mm) in 15 mL of pyridine was treated with 1,3-dimethoxybenzene (2.5 g, 18.1 mm) over a period of 5 min. The resulting mixture was then refluxed for 4 h. to give the crude 1-dibromophosphino-2,4dimethoxybenzene (³¹P NMR: δ159.2 ppm). This compound was used directly for the next step without further purification. Next, polymer-supported secondary amines from Example 1 (10.0 g, 1.1 mmol/g, 11.0 mmol) was slowly added into the mixture above while stirring at room temperature for a period of 10 min. The resulting suspension was stirred at room temperature overnight before the solution was filtered off. The resin was washed with THF (50 mL), hexane (3×50 mL), CH₂Cl₂ (4×50 mL), and hexane (2×50 mL). The resulting resin was dried in vacuum overnight to yield the polymer-supported 2-P(Br)-1,5-(MeO)₂-C₆H₃. ³¹P NMR (122 MHz, CDCl₃): δ153.8 ppm.

Example 21

Polymer-Bound 2-P(Ph)-1,5-(MeO)₂C₆H₃

A suspension of polymer-bound 2-P(Br)-1,5-(MeO)₂-C₆H₃ (2.0 g, 1.82 mmol, 0.908 mm/g) from Example 20, and PhMgBr (12.0 mmol, 1.0 M in THF solution) in 10 mL of THF was refluxed overnight before the solution was filtered off. The resulting resin was washed with THF (3×20 mL), CH₂Cl₂ (3×10 mL), Me₂CHOH (2×10 mL), THF/H₂O (70/30 volume ratio, 2×20 mL) and hexane (3×10 mL). The resin was dried in vacuum overnight. ³¹P NMR (122 MHz, CDCl₃): δ56.9 ppm.

Example 22

Polymer-Bound 2-P(i-Pr)-1,5-(MeO)₂C₆H₃

A suspension of polymer-bound 2-P(Br)-1,5-(MeO)₂—C₆H₃ (2.0 g, 1.82 mmol, 0.908 mm/g) from Example 20, and i-PrMgBr (12.0 mmol, 1.0 M in THF solution) in 10 mL of THF was refluxed overnight before the solution was filtered off. The resulting resin was washed with THF (3×20 mL), CH$_2$Cl$_2$ (3×10 mL), Me$_2$CHOH (2×10 mL), THF/H$_2$O (70/30 volume ratio, 2×20 mL) and hexane (3×10 mL). The resin was dried in vacuum overnight. $^{31}$P NMR (122 MHz, CDCl$_3$): δ60.7 ppm.

Example 23

Polymer-Bound 2-P(2,4,6-(Me)$_3$C$_6$H$_2$)-1,5-(MeO)$_2$C$_6$H$_3$

A suspension of polymer-bound 2-P(Br)-1,5-(MeO)$_2$C$_6$H$_3$ (1.0 g, 0.908 mmol, 0.908 mm/g) from Example 20, and 2,4,6-(Me)$_3$C$_6$H$_2$MgBr (12.0 mmol, 1.0 M in THF solution) in 10 mL of THF was refluxed overnight before the solution was filtered off. The resulting resin was washed with THF (3×20 mL), CH$_2$Cl$_2$ (3×10 mL), Me$_2$CHOH (2×10 mL), THF/H$_2$O (70/30 volume ratio, 2×20 mL) and hexane (3×10 mL). The resin was dried in vacuum overnight. $^{31}$P NMR (122 MHz, CDCl$_3$): δ53.5 ppm.

Example 24

Polymer-Bound 2-P(Cy)-1,5-(MeO)$_2$C$_6$H$_3$

A suspension of polymer-bound 2-P(Br)-1,5-(MeO)$_2$—C$_6$H$_3$ (1.0 g, 0.908 mmol, 0.908 mm/g) from Example 20, and CyMgBr (12.0 mmol, 1.0 M in THF solution) in 10 mL of THF was refluxed overnight before the solution was filtered off. The resulting resin was washed with THF (3×20 mL), CH$_2$Cl$_2$ (3×10 mL), Me$_2$CHOH (2×10 mL), THF/H$_2$O (70/30 volume ratio, 2×20 mL) and hexane (3×10 mL). The resin was dried in vacuum overnight. $^{31}$P NMR (122 MHz, CDCl$_3$): δ57.1 ppm.

Example 25

Polymer-Bound 2-P(Br)-1,3,5-(MeO)$_3$C$_6$H$_2$

A solution of PBr$_3$ (8.0 g, 29.6 mm) in 150 mL of pyridine was treated with 1,3,5-trimethoxybenzene (5.0 g, 29.7 mm) over a period of 5 min. The resulting mixture was then refluxed overnight to give the crude 1-dibromo-phosphino-2,4,6-trimethoxybenzene ($^{31}$P NMR: δ143.7 ppm). This compound was used directly for the next step without further purification. Next, polymer-supported secondary amines from Example 1 (5.0 g, 1.1 mmol/g, 5.5 mmol) was slowly added into the mixture above while stirring at room temperature for a period of 10 min. The resulting suspension was refluxed overnight before the solution was filtered off. The resin was washed with THF (2×50 mL), hexane (3×50 mL), CH$_2$Cl$_2$ (4×50 mL), and hexane (2×50 mL). The resulting resin was dried in vacuum overnight to yield the polymer-supported 2-P(Br)-1,3,5-(MeO)$_3$C$_6$H$_2$. $^{31}$P NMR (202 MHz, CDCl$_3$): δ170.9 ppm.

Results from Examples 20–25 are shown in Table 5 below.

TABLE 5

Polymer-Supported Synthetic Results of PC$_2$O Ligands

| Example | Product | $^{31}$P NMR | Example | Product | $^{31}$P NMR |
|---------|---------|--------------|---------|---------|--------------|
| 20 | [P-N-propyl-P(Br)-(2-OMe,4-OMe-C$_6$H$_3$)] | 153.8 | 23 | [P-N-propyl-P(mesityl)-(2-OMe,4-OMe-C$_6$H$_3$)] | 53.5 |
| 21 | [P-N-propyl-P(Ph)-(2-OMe,4-OMe-C$_6$H$_3$)] | 56.9 | 24 | [P-N-propyl-P(Cy)-(2-OMe,4-OMe-C$_6$H$_3$)] | 57.1 |

TABLE 5-continued

Polymer-Supported Synthetic Results of PC$_3$O Ligands

| Example | Product | $^{31}$P NMR | Example | Product | $^{31}$P NMR |
|---------|---------|--------------|---------|---------|--------------|
| 22 | (structure) | 60.7 | 25 | (structure) | 170.9 |

Synthesis of Polymer-Supported P—C$_3$—O Ligands

Example 26

Polymer-Bound P(Ph)CH$_2$CH(Et)CH$_2$OCH$_2$Ph

A mixture of PhCH$_2$OCH$_2$CH=CH$_2$ (6.0 g, 40.1 mm) and Cp$_2$ZrCl$_2$ (0.2 g, 0.75 mm) (Cp=cyclopentadienyl) in 20 mL of THF was treated with EtMgBr (20.0 mm, 2 M solution in THF) dropwise over a period of 5 min. The resulting reaction solution was stirred at room temperature for 4 days before polymer-supported P(Ph)Cl (3.0 g, 3.0 mm, 1.00 mm/g, prepared as Example 1 using Me$_3$CNH$_2$ in place of the n-propylamine) was added into the reaction solution above. The resulting suspension was stirred at room temperature for 2 days before the solution was filtered off. The resulting resin was washed with THF (3×20 mL), CH$_2$Cl$_2$ (3×10 mL), Me$_2$CHOH (2×10 mL) and hexane (3×10 mL). The resin was dried in vacuum overnight. $^{31}$P NMR (122 MHz, CDCl$_3$): δ55.7 ppm.

Example 27

Polymer-Bound P(Ph)CH$_2$CH(Et)CH$_2$OCH$_2$CH$_2$CH$_2$CH$_3$

A mixture of CH$_3$CH$_2$CH$_2$CH$_2$OCH$_2$CH=CH$_2$ (5.0 g, 42.9 mm) and Cp$_2$ZrCl$_2$ (0.2 g, 0.75 mm) in 20 mL of THF was treated with EtMgBr (20.0 mm, 2 M solution in THF) dropwise over a period of 5 min. The resulting reaction solution was stirred at room temperature for 4 days before the polymer-supported P(Ph)Cl (3.0 g, 3.0 mm, 1.00 mm/g, prepared as Example 1 using Me$_3$CNH$_2$ in place of the n-propylamine) was added into the reaction solution above. The resulting suspension was stirred at room temperature for 2 days before the solution was filtered off. The resulting resin was washed with THF (3×20 mL), CH$_2$Cl$_2$ (3×10 mL), Me$_2$CHOH (2×10 mL) and hexane (3×10 mL). The resin was dried in vacuum overnight. $^{31}$P NMR (122 MHz, CDCl$_3$): δ56.0 ppm.

Cleavage of Ligands from the Polymer-Bound Compounds

Example 28

Synthesis of (C$_4$H$_3$O)PH(O)(C$_4$H$_3$S)

A suspension of polymer-bound P(C$_4$H$_3$O)(C$_4$H$_3$S) (1.0 g, 0.899 mmol, 0.899 mm/g, prepared as in Example 4) and H$_2$O (0.5 g, 28 mm) in 10 mL of THF was refluxed overnight before the resin was filtered off and washed with hexane (3×10 mL). Removal of solvents and excess H$_2$O from the filtrates by vacuum afforded 16 mg (15% yield) of (C$_4$H$_3$O)PH(O)(C$_4$H$_3$S). It was >95% pure by $^1$H NMR and GC/MS. $^{31}$P NMR (121 MHz, CDCl$_3$): δ–6.7 ppm. $^{31}$P NMR ($^1$H-coupled, 121 MHz, CDCl$_3$): δ–6.7 (d, J$_{P-H}$=515.5 Hz) ppm. $^1$H NMR (500 MHz, CDCl$_3$): δ8.25 (d, J$_{P-H}$=515.5 Hz, 1H), 7.7–7.6 (m, 3H), 7.19 (s, 1H), 6.5 (s, 1H). $^{13}$C NMR (125 MHz, CDCl$_3$): δ148.5 (d, J$_{p-c}$=8.3 Hz), 136.1 (d, J$_{p-c}$=12.3 Hz), 134.3 (d, J$_{p-c}$=5.7 Hz), 128.3 (d, J$_{p-c}$=15.1 Hz), 122.4 (d, J$_{p-c}$=21.8 Hz). 110.9 (d, J$_{p-c}$=9.1 Hz).

Example 29

Synthesis of 2-PCl(Br)-1-NMe$_2$-4-(Me)C$_6$H$_3$

A suspension of polymer-bound 2-P(Br)-1-NMe$_2$-4-MeC$_6$H$_3$ (10.0 g, 8.4 mmol, 0.84 mm/g, prepared as in Example 5) and PCl$_3$ (7.0 g, 51.0 mmol) in THF (100 mL) was stirred overnight at room temperature before the resin was filtered off and washed with hexane (2×25 mL). Removal of solvents and excess PCl$_3$ from the filtrates by vacuum afforded 1.5 g (64% yield) of crude 2-PCl(Br)-1-NMe$_2$-4-MeC$_6$H$_3$. It was >95% pure by $^1$H NMR and GC/MS. $^{31}$P NMR(121 MHz, CDCl$_3$): δ149.4 (s) ppm. $^1$H NMR(500 MHz, CDCl$_3$): δ7.71 (s, 1H), 7.24 (m, 2H), 2.72 (s, 6H), 2.29 (s, 3H). $^{13}$C NMR (125 MHz, CDCl$_3$): δ138.3, 137.5, 137.1, 134.7, 131.6, 121.7, 46.4, 21.2 ppm.

Example 30

Synthesis of 2-PCl(Ph)-1-NMe₂-4-(Me)C₆H₃

A suspension of polymer-bound 2-P(Ph)-1-NMe₂-4-(Me)C₆H₃ (10.0 g, 9.1 mmol, 0.91 mm/g, prepared as in Example 7) and PCl₃ (6.6 g, 48.0 mmol) in THF (100 mL) was stirred overnight at room temperature before the resin was filtered off and washed with hexane (2×25 mL). Removal of solvents and excess PCl₃ from the filtrates by vacuum afforded 1.4 g (92% yield) of crude 2-PCl(Ph)-1-NMe₂-4-(Me)C₆H₃. It was >95% pure by $^1$H NMR and GC/MS. $^{31}$P NMR (121 MHz, CDCl₃): δ73.1 (s) ppm. $^1$H NMR (500 MHz, CDCl₃): δ7.83–7.16 (m, 8H), 2.50 (s, 3H), 2.35 (s, 6H). $^{13}$C NMR (125 MHz, CDCl₃): δ137.1, 132.3, 132.1, 132.0, 131.4, 129.9, 128.4, 121.6, 45.4, 21.5. ppm. HRMS: Calcd for C₁₅H₁₇PNCl(M⁺): 277.0787. Found: 277.0789.

Example 31

Synthesis of 2-PH(O)(Ph)-1-NMe₂-4-(Me)C₆H₃

A suspension of polymer-bound 2-P(Ph)-1-NMe₂-4-MeC₆H₃ (2.0 g, 1.8 mmol, 0.91 mm/g, prepared as in Example 7) and H₂O (0.5 g, 28 mm) in 10 mL of THF was refluxed overnight before the resin was filtered off and washed with hexane (3×10 mL). Removal of solvents and excess H₂O from the filtrates by vacuum afforded 400 mg (85% yield) of crude 2-PH(O)(Ph)-1-NMe₂-4-(Me)C₆H₃. It was >95% pure by $^1$H NMR and GC/MS. $^{31}$P NMR (121 MHz, CDCl₃): δ19.2 (s), 19.1 (s) ppm. $^{31}$P NMR ($^1$H-coupled, 121 MHz, CDCl₃): δ19.2 (d, J$_{P-H}$=498.9 Hz), δ19.1 (d, J$_{P-H}$=498.9 Hz) ppm. $^1$H NMR (500 MHz, CDCl₃): δ8.09 (d, J$_{P-H}$=499.1 Hz, 1H), 7.60–7.04 (m, 8H), 2.37 (s, 6H), 2.25 (s, 3H). $^{13}$C NMR (125 MHz, CDCl₃): δ155.0, 135.2, 134.6, 133.6, 133.5, 131.7, 130.5, 128.4, 128.3, 122.0, 45.9, 20.9, ppm. HRMS: Calcd for C₁₅H₁₈PNO(M⁺): 259.1126. Found: 259.1146.

Example 32

Synthesis of 2-PH(O)(i-Pr)-1-NMe₂-4-(Me)C₆H₃

A suspension of polymer-bound 2-P(Br)-1-NMe₂-4-MeC₆H₃ (12.0 g, 10.0 mmol, 0.84 mm/g, prepared as in Example 5) and i-PrMgCl (240.0 mmol, 2.0 M in THF solution) in 200 mL of THF was stirred at room temperature for 1 h, then refluxed overnight before the solution was filtered off. The resulting resin was washed with THF (3×50 mL), CH₂Cl₂ (3×50 mL), Me₂CHOH (2×30 mL), THF/H₂O (70/30 volume ratio, 2×40 mL) and hexane (3×80 mL). The suspension of resin above and H₂O (3.0 g, 166.7 mm) in 200 mL of THF was refluxed overnight before the resin was filtered off and washed with hexane (3×20 mL). Removal of solvents and excess H₂O from the filtrates by vacuum afforded 820 mg (36% yield) of crude 2-PH(O)(i-Pr)-1-NMe₂-4-(Me)C₆H₃. It was >95% pure by $^1$H NMR and GC/MS. $^{31}$P NMR (121 MHz, CDCl₃): δ37.9 (s) ppm. $^{31}$P NMR ($^1$H-coupled, 121 MHz, CDCl₃): δ37.9 (d, J$_{P-H}$=472.7 Hz) ppm. $^1$H NMR (500 MHz, CDCl₃): δ7.50 (d, J=13.47 Hz, 1H), 7.31 (d, J$_{P-H}$=472.8 Hz, 1H), 7.23 (d, J=8.06 Hz, 1H), 7.11 (m, 1H), 2.58 (s, 6H), 2.25 (s, 3H), 1.05 (m, 6H) ppm. $^{13}$C NMR (125 MHz, CDCl₃): δ154.2, 134.3, 133.7, 133.4, 125.9, 120.8, 45.7, 27.2, 20.4, 15.9, 14.4 ppm.

Results from Examples 28–32 are shown in Table 6 below.

TABLE 6

| Example | Substrate | $^{31}$P NMR (ppm) | Product | $^{31}$P NMR (ppm) | Isolated Yield (%) |
|---|---|---|---|---|---|
| 28 | (polymer-bound N-P(thienyl)(furyl) aryl NMe₂/Me substrate) | | (O=PH(thienyl)(furyl)) | −6.7 | 15 |

TABLE 6-continued

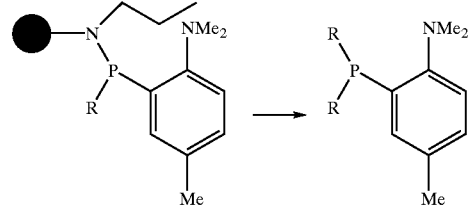

| Example | Substrate | 31P NMR (ppm) | Product | 31P NMR (ppm) | Isolated Yield (%) |
|---|---|---|---|---|---|
| 29 | 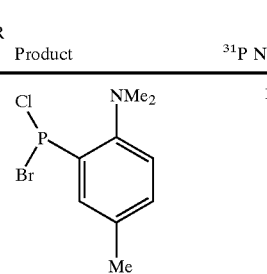 | 156.1 | 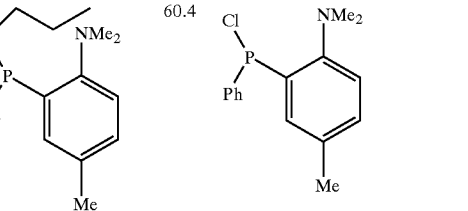 | 149.4 | 65 |
| 30 |  | 60.4 | 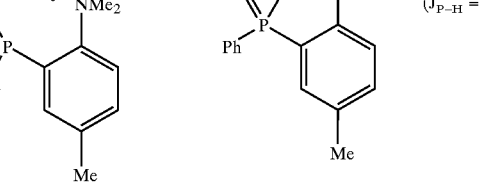 | 73.1 | 92 |
| 31 |  | 60.4 | 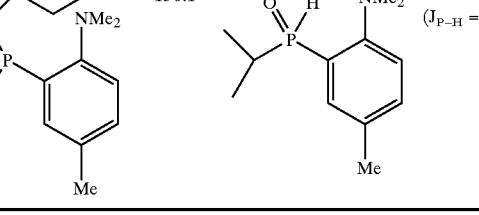 | 19.3 ($J_{P-H}$ = 498.9 Hz) | 85 |
| 32 | 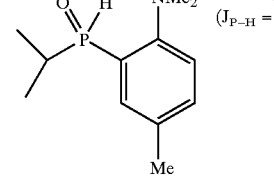 | 156.1 | | 37.9 ($J_{P-H}$ = 472.7 Hz) | 36 |

Example 33

Synthesis of 1-PhP(Cl)-2,4-(MeO)$_2$C$_6$H$_3$

A suspension of polymer-bound 1-PPh-2,4-(MeO)$_2$C$_6$H$_3$ (2.0 g, 0.85 mmol/g, 1.70 mmol) from Example 21 and PCl$_3$ (1.3 g, 9.49 mmol) in 15 mL of THF was stirred overnight at room temperature before the resin was filtered off and washed with hexane (2×10 mL). Removal of solvents and excess PCl$_3$ from the filtrates by vacuum afforded 450 mg (94% yield) of crude 1-PhP(Cl)-2,4-(MeO)$_2$C$_6$H$_3$. It was >95% pure by $^1$H NMR and GC/MS. $^{31}$P NMR (202 MHz, CDCl$_3$): δ78.8 ppm. $^1$H NMR (500 MHz, CDCl$_3$): δ7.43 (m, 2H), 7.22 (m, 4H), 6.38 (m, 1H), 6.27 (m, 1H), 3.62 (s, 3H), 3.55 (s, 3H). $^{13}$C NMR(125 MHz, CDCl$_3$): δ163.4, 162.0, 139.0, 133.2, 131.5, 129.9, 128.2, 117.4, 105.7, 98.3, 55.7, 55.3, HRMS: Calcd for C$_{14}$H$_{14}$PClO$_2$(M$^+$): 280.0420. Found: 280.0421.

Example 34

Synthesis of 2-PH(O)(i-Pr)-1,5-(MeO)$_2$C$_6$H$_3$

A suspension of polymer-bound 2-P(i-Pr)-1,5-(MeO)$_2$C$_6$H$_3$ (2.0 g, 1.876 mmol, 0.938 mm/g) from Example 22, and H$_2$O (0.5 g, 28 mm) in 10 mL of THF was refluxed overnight before the resin was filtered off and washed with hexane (3×10 mL). Removal of solvents and excess H$_2$O from the filtrates by vacuum afforded 100 mg (23% yield) of 2-PH(O)(i-Pr)-1,5-(MeO)$_2$—C$_6$H$_3$. It was >95% pure by $^1$H NMR and GC/MS. $^{31}$P NMR (202 MHz, CDCl$_3$): δ35.8 (s) ppm. $^{31}$P NMR ($^1$H-coupled, 202 MHz, CDCl$_3$): δ35.8 (d, $J_{P-H}$=485.8 Hz) ppm. $^1$H NMR (500 MHz, CDCl$_3$): δ7.57 (m, 1H), 7.25 (d, $J_{P-H}$=485.2 Hz, 1H), 6.48 (m, 1H), 6.37 (m, 1H), 3.76 (d, J=15.2 Hz, 3H), 3.70 (d, J=38.7 Hz, 3H), 2.18 (m, 1H), 1.12-0.81 (m, 6H). $^{13}$C NMR (125 MHz, CDCl$_3$):

165.0, 161.8, 135.1, 105.6, 105.5, 98.2, 67.9, 55.6, 27.4, 14.5 ppm. MS: 229.2 (M+1).

Example 35

Synthesis of (+/−)-2,5-Me$_2$—C$_4$H$_6$-1-N(2'-PhPH(O)-4'-Me)C$_6$H$_3$

A suspension of polymer-bound (+/−)-2,5-Me$_2$-C$_4$H$_6$-1-N(2'-PPh-4'-Me)C$_6$H$_3$ (1.0 g, 0.87 mmol, 0.87 mm/g) from Example 15, and H$_2$O (0.5 g, 28 mm) in 10 mL of THF was refluxed overnight before the resin was filtered off and washed with hexane (3×10 mL). Removal of solvents and excess H$_2$O from the filtrates by vacuum afforded 75 mg (28% yield) of (+/−)-2,5-Me$_2$—C$_4$H$_6$-1-N(2'-PhPH(O)-4'-Me)C$_6$H$_3$. It was >95% pure by $^1$H NMR and GC/MS. $^{31}$P NMR (202 MHz, CDCl$_3$): δ23.6 (s) ppm. $^{31}$P NMR ($^1$H-coupled, 202 MHz, CDCl$_3$): δ23.6 (d, J$_{P-H}$=484.6 Hz) ppm. $^1$H NMR (500 MHz, CDCl$_3$): δ7.97 (d, J$_{P-H}$=484.6 Hz, 1H), 7.57–7.20 (m, 7H), 6.90 (m, 1H), 3.87 (m, 1H), 3.44 (m, 1H), 2.31 (s, 3H), 1.96–1.82 (m, 2H), 1.24–1.11 (m, 2H), 0.62 (d, J=6.44 Hz, 3H), 0.33 (d, J=5.89 Hz, 3H). $^{13}$C NMR (125 MHz, CDCl$_3$): δ148.1, 134.6, 134.5, 133.8, 131.4, 130.6, 130.5, 128.2, 128.1, 124.7, 60.3, 53.1, 32.1, 31.5, 20.7, 18.3, 17.9 ppm.

Example 36

Synthesis of (+/−)-2,5-Me$_2$—C$_4$H$_6$-1-N(2'-MePH(O)-4'-Me)C$_6$H$_3$

A suspension of polymer-bound (+/−)-2,5-Me$_2$—C$_4$H$_6$-1-N(2'-PMe-4'-Me)C$_6$H$_3$ (1.0 g, 0.918 mmol, 0.918 mm/g) from Example 16, and H$_2$O (0.5 g, 28 mm) in 10 mL of THF was refluxed overnight before the resin was filtered off and washed with hexane (3×10 mL). Removal of solvents and excess H$_2$O from the filtrates by vacuum afforded 78 mg (34% yield) of (+/−)-2,5-Me$_2$-C$_4$H$_6$-1-N(2'-MePH(O)-4'-Me)C$_6$H$_3$. It was >95% pure by $^1$H NMR and GC/MS. $^{31}$P NMR (202 MHz, CDCl$_3$): δ26.4 (s) ppm. $^{31}$P NMR ($^1$H-coupled, 202 MHz, CDCl$_3$): δ26.4 (d, J$_{P-H}$=477.5 Hz) ppm. $^1$H NMR (500 MHz, CDCl$_3$): δ7.47 (d, J$_{P-H}$=476.3 Hz, 1H), 7.40 (m, 1H), 67.21 (m, 1H), 6.99 (m, 1H), 4.06 (m, 1H), 3.66 (m, 1H), 2.26 (s, 3H), 2.15–2.04 (m, 2H), 1.78 (dd, J=3.77 Hz, 3H). $^{13}$C NMR(125 MHz, CDCl$_3$): δ147.6, 133.4, 133.3, 132.9, 132.8, 124.4, 60.6, 58.2, 32.5, 31.8, 20.6, 19.5, 17.9, 15.8, 15.2 ppm.

Example 37

Synthesis of Chiral (S, S)-2,5-(Me$_2$)C$_4$H$_6$-1-N(4'-PH(O)Ph)C$_6$H$_4$

A suspension of polymer-bound Chiral (S, S)-2,5-(Me$_2$) C$_4$H$_6$-1-N(4'-PPh)C$_6$H$_4$ (0.8 g, 0.703 mmol, 0.879 mm/g) from Example 19, and H$_2$O (0.5 g, 28 mm) in 10 mL of THF was refluxed overnight before the resin was filtered off and washed with hexane (3×10 mL). Removal of solvents and excess H$_2$O from the filtrates by vacuum afforded 74 mg (37% yield) of Chiral (S, S)-2,5-(Me$_2$)C$_4$H$_6$-1-N(4'-PH(O)Ph)C$_6$H$_4$. It was >95% pure by $^1$H NMR and GC/MS. $^{31}$P NMR (202 MHz, CDCl$_3$): δ23.3 (s) ppm. $^{31}$P NMR ($^1$H-coupled, 202 MHz, CDCl$_3$): δ23.3 (d, J$_{P-H}$=474.2 Hz) ppm. $^1$H NMR (500 MHz, CDCl$_3$): δ7.79 (d, J$_{P-H}$=518.2 Hz, 1H), 7.66–6.52 (m, 9H), 3.96 (m, 2H), 2.16 (m, 2H), 1.60 (m, 2H), 1.04 (d, J=6.20 Hz, 6H) ppm. $^{13}$C NMR (125 MHz, CDCl$_3$): δ148.4, 133.2, 132.2, 131.9, 130.8, 128.6, 113.2, 113.0, 53.1, 30.1, 17.9 ppm. MS: 300.2 (M+1).

Example 38

Synthesis of PhP(Cl)CH$_2$CH(Et)CH$_2$OCH$_2$CH$_2$CH$_2$CH$_3$

A suspension of polymer-bound P(Ph)CH$_2$CH(Et)CH$_2$OCH$_2$CH$_2$CH$_2$CH$_3$ (3.0 g, 3.0 mmol, 1.00 mm/g) from Example 27, and PCl$_3$ (1.3 g, 9.49 mmol) in 20 mL of THF was stirred overnight at room temperature before the resin was filtered off and washed with hexane (2×10 mL). Removal of solvents and excess PCl$_3$ from the filtrates by vacuum afforded 640 mg (74% yield) of PCl(Ph)CH$_2$CH(Et)CH$_2$OCH$_2$Ph. It was >95% pure by $^1$H NMR and GC/MS. $^{31}$P NMR (202 MHz, CDCl$_3$): δ93.9 (s) ppm. $^1$H NMR (500 MHz, CDCl$_3$): δ7.57 (2H), 7.26 (3H), 3.19 (m, 4H), 2.13–1.93 (m, 2H), 1.39–1.18 (m, 7H), 0.76 (m, 6H) ppm. $^{13}$C NMR (125 MHz, CDCl$_3$): δ139.6, 131.6, 131.2, 128.7, 74.0, 71.0, 40.2, 37.5, 31.9, 25.8, 19.5, 14.1, 11.3 ppm. HRMS: Calcd for C$_{15}$H$_{24}$PClO (M$^+$): 286.1253. Found: 286.1257.

Example 39

Synthesis of PhPH(O)CH$_2$CH(Et)CH$_2$OCH$_2$Ph

A suspension of polymer-bound P(Ph)CH$_2$CH(Et)CH$_2$OCH$_2$Ph (3.0 g, 3.0 mmol, 1.00 mm/g) from Example 26, and H$_2$O (0.5 g, 28 mm) in 15 mL of THF was refluxed overnight before the resin was filtered off and washed with hexane (3×10 mL). Removal of solvents and excess H$_2$O from the filtrates by vacuum afforded 620 mg (68% yield) of. PhPH(O)CH$_2$CH(Et)CH$_2$OCH$_2$Ph. It was >95% pure by $^1$H NMR and GC/MS. $^{31}$P NMR (202 MHz, CDCl$_3$): δ26.8 (s), 26.6 (s) ppm. $^{31}$P NMR ($^1$H-coupled, 202 MHz, CDCl$_3$): δ26.8 (d, J$_{P-H}$=470.0 Hz), 26.6 (d, J$_{P-H}$=469.0 Hz) ppm. $^1$H NMR (500 MHz, CDCl$_3$): δ7.51–7.05 (m, 10H), 7.39 (d, J$_{P-H}$=469.6 Hz), 7.34 (d, J$_{P-H}$=471.4 Hz), 4.30 (m, 1H), 4.20 (s, 1H), 3.42–3.21 (m, 2H), 2.00-1.28 (m, 5H), 0.68 (m, 3H) ppm. $^{13}$C NMR(125 MHz, CDCl$_3$): δ138.0, 131.9, 131.6, 129.6, 129.4, 128.5, 128.0, 127.3, 72.7, 72.0, 34.7, 32.6, 25.0, 10.8 ppm. HRMS: Calcd for C$_{18}$H$_{23}$PO$_2$(M$^+$): 302.1436. Found: 302.1430.

Synthesis of Aryl Sulfides from Aryl Halides Using Cleaved Ligand Coordinated Palladium Catalysts

Example 40

General Procedure for Pd Catalyzed Cross-Coupling of Aryl Halides with Thiols

In the drybox, 52.0 mg (0.184 mmol) of (Me$_2$CH)PH(O) (2,4-(MeO)$_2$C$_6$H$_3$) from Example 34, 34.0 mg (0.151 mmol) of Pd(OAc)$_2$ and 14.0 ml of toluene were loaded into a reactor (20 ml) equipped with a magnetic stir bar. The resulting mixture was stirred at room temperature for 1 h. Next, 576.0 mg (6.0 mmol) of NaOtBu, 816.0 mg (4.0 mmol) of PhI and 360 mg (4.0 mmol) of HS-t-Bu were added into the mixture above, The resulting mixture was refluxed for 3 days. The reaction mixture was then cooled to room temperature, chromatographed on silicon gel using ethyl acetate/hexane (5% volume ratio) as eluant. The eluate was concentrated by rotary evaporation followed by high vacuum to yield 190 mg (29% yield) of t-butyl phenyl sulfide. It was >95% pure by $^1$H NMR and GC/MS. $^1$H NMR (500 MHz, CDCl$_3$): δ7.43–7.42 (m, 2H), 7.22–7.19 (m, 3H), 1.17 (s, 9H) ppm. $^{13}$C NMR (125 MHz, CDCl$_3$): δ137.4, 132.7, 128.5, 128.3, 30.9 ppm.

Example 41

In the drybox, 51.0 mg (0.226 mmol) of (Me$_2$CH)PH(O) (1-NMe$_2$-4-Me—C$_6$H$_3$) from Example 32, 34.0 mg (0.151 mmol) of Pd(OAc)$_2$ and 4.0 ml of toluene were loaded into a reactor (20 ml) equipped with a magnetic stir bar. The resulting mixture was stirred at room temperature for 1 h.

Next, 216.0 mg (2.25 mmol) of NaOtBu, 314.0 mg (2.0 mmol) of PhBr and 135 mg (1.5 mmol) of HS-t-Bu were added into the mixture above, The resulting mixture was refluxed for 18 h. The reaction mixture was then cooled to room temperature, chromatographed on silicon gel using ethyl acetate/hexane (5% volume ratio) as eluant. The eluate was concentrated by rotary evaporation followed by high vacuum to yield 126 mg (51% yield) of t-butyl phenyl sulfide. It was >95% pure by $^1$H NMR and GC/MS. $^1$H NMR (500 MHz, CDCl$_3$): δ7.43–7.42 (m, 2H), 7.22–7.19 (m, 3H), 1.17 (s, 9H) ppm. $^{13}$C NMR (125 MHz, CDCl$_3$): δ137.4, 132.7, 128.5, 128.3, 30.9 ppm.

What is claimed is:

1. The process to prepare a supported phosphine compound of the structure of Formula 1 A:

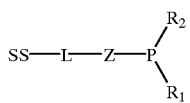

1A the process comprising the steps of:
 a) contacting a phosphine of the formula XPR$_1$R$_2$, wherein X is a halogen, with the solid support, resulting in the P in the phosphine attached indirectly or directly to the solid support via a covalent bond, and
 b) optionally, replacing one or more of R$_1$ or R$_2$ with any other R$_1$ or R$_2$ respectively, wherein:
  SS is a polymer solid support;
  R$_1$ is selected from the group consisting of halogen, hydrocarbyl, substituted hydrocarbyl, heterocyclic and substituted heterocyclic;
  R$_2$ is selected from the group consisting of halogen, cyclic hydrocarbyl, substituted cyclic hydrocarbyl, heterocyclic and substituted heterocyclic;
  Z is a divalent or trivalent attaching group covalently attached to at least one phosphorus in the phosphine, selected from the group consisting of hydrocarbylene, substituted hydrocarbylene, —O—, —S—, and —NQ—, where Q is selected from the group consisting of an optionally-substituted hydrocarbyl and halogen; and
  L is a divalent linking group covalently attached to Z and to SS, selected from the group consisting of optionally-substituted chains of from 1 to 12 linear, branched, and cyclic carbon atoms.

2. The process of claim 1 wherein SS is selected from the group consisting of polyolefins, polyacrylates, polymethacrylates, and copolymers thereof.

3. The process of claim 1 wherein SS is polystyrene;
 L is —CH$_2$—;
 Z is —(NQ)—;
 Q is selected from the group consisting of n-propyl, and t-butyl;
 R$_1$ is selected from the group consisting of bromo, chloro, phenyl, methyl, i-propyl, mesityl, cyclohexyl, 3-methylphenyl, 2-methoxyphenyl, 12,4,6-trimethoxyphenyl, 2-furanyl, 2-thienyl, —CH$_2$CH(C$_2$H$_5$)CH$_2$O(CH$_2$)$_3$CH$_3$, and —CH$_2$CH(C$_2$H$_5$)CH$_2$OCH$_2$C$_6$H$_5$;
 R$_2$ is selected from the group consisting of phenyl, 2-furanyl, 2-(5-methylfuranyl), 2-thienyl, 2-N,N-dimethyl-5-toluidinyl, 4-pyrrolidino-3-pyridinyl, 2-[(2,5-dimethyl)-1-pyrrolidinyl]-4-methylphenyl, p-[(2,5-dimethyl)-1-pyrrolidinyl]phenyl, and 2,4-dimethoxyphenyl.

4. The supported phosphine compound of the structure of Formula 1A:

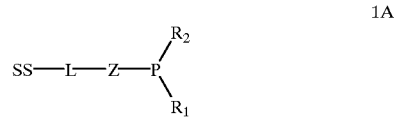

1A wherein:
 SS is a polymer solid support;
 R$_1$ is selected from the group consisting of halogen, hydrocarbyl, substituted hydrocarbyl, heterocyclic and substituted heterocyclic;
 R$_2$ is selected from the group consisting of halogen, cyclic hydrocarbyl, substituted cyclic hydrocarbyl, heterocyclic and substituted heterocyclic;
 Z is a divalent or trivalent attaching group covalently attached to at least one phosphorus in the phosphine, selected from the group consisting of hydrocarbylene, substituted hydrocarbylene, —O—, —S—, and —NQ—, where Q is selected from the group consisting of an optionally-substituted hydrocarbyl and halogen; and
 L is a divalent linking group covalently attached to Z and to SS, selected from the group consisting of optionally-substituted chains of from 1 to 12 linear, branched, and cyclic carbon atoms.

5. The supported phosphine compound of claim 4 wherein SS is selected from the group consisting of polyolefins, polyacrylates, polymethacrylates, and copolymers thereof.

6. The supported phosphine compound of claim 4 wherein SS is polystyrene;
 L is —CH$_2$—;
 Z is —(NQ)—;
 Q is selected from the group consisting of n-propyl, and t-butyl;
 R$_1$ is selected from the group consisting of bromo, chioro, phenyl, methyl, i-propyl, mesityl, cyclohexyl, 3-methylphenyl, 2-methoxyphenyl, 12,4,6-trimethoxyphenyl, 2-furanyl, 2-thienyl, —CH$_2$CH(C$_2$H$_5$)CH$_2$O(CH$_2$)$_3$CH$_3$, and —CH$_2$CH(C$_2$H$_5$)CH$_2$OCH$_2$C$_6$H$_5$;
 R$_2$ is selected from the group consisting of phenyl, 2-furanyl, 2-(5-methylfuranyl), 2-thienyl, 2-N,N-dimethyl-5-toluidinyl, 4-pyrrolidino-3-pyridinyl, 2-[(2,5-dimethyl)-1-pyrrolidinyl]-4-methylphenyl, p-[(2,5-dimethyl)-1-pyrrolidinyl]phenyl, and 2,4-dimethoxyphenyl.

\* \* \* \* \*